US012108985B2

(12) United States Patent
Maher et al.

(10) Patent No.: US 12,108,985 B2
(45) Date of Patent: Oct. 8, 2024

(54) FLUID MANAGEMENT SYSTEM WITH INTEGRATED LASER FIBER COOLING

(71) Applicant: BOSTON SCIENTIFIC SCIMED, INC., Maple Grove, MN (US)

(72) Inventors: Michelle Maher, Tipperary (IE); Lee Smith, Waterford (IE); William Stanhope, Lunenburg, MA (US); Nishant Khattar, White Bear Township, MN (US); Eric Wong, South Grafton, MA (US); Niraj Prasad Rauniyar, Plymouth, MN (US); Logan Ernster, Minneapolis, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 213 days.

(21) Appl. No.: 17/388,535

(22) Filed: Jul. 29, 2021

(65) Prior Publication Data
US 2022/0031392 A1    Feb. 3, 2022

Related U.S. Application Data

(60) Provisional application No. 63/058,687, filed on Jul. 30, 2020.

(51) Int. Cl.
*A61B 18/22*      (2006.01)
*A61B 18/00*      (2006.01)

(52) U.S. Cl.
CPC .... *A61B 18/22* (2013.01); *A61B 2018/00678* (2013.01); *A61B 2018/00714* (2013.01);
(Continued)

(58) Field of Classification Search
CPC ............ A61B 18/22; A61B 2018/2253; A61B 2018/00714; A61B 2018/00744; A61N 2005/002; A61N 2005/0025
(Continued)

(56) References Cited

U.S. PATENT DOCUMENTS

| 4,655,197 A | 4/1987 | Atkinson |
| 4,902,276 A | 2/1990 | Zakko |

(Continued)

FOREIGN PATENT DOCUMENTS

| JP | 2001079016 A | 3/2001 |
| JP | 2002113036 A | 4/2001 |

(Continued)

OTHER PUBLICATIONS

International Search Report and Written Opinion dated Nov. 26, 2021 for Internal Application No. PCT/US2021/043656.

*Primary Examiner* — Ahmed M Farah
(74) *Attorney, Agent, or Firm* — Seager, Tufte & Wickhem, LLP

(57) ABSTRACT

A medical system may include: a medical device including an elongate shaft configured to access a treatment site within a patient and a handle coupled to a proximal end of the elongate shaft; a laser device including an elongate tubular member configured for insertion through a working lumen of the medical device, the elongate tubular member including a cooling channel and a laser fiber extending distally within the cooling channel; and a fluid management system including an inflow pump configured to pump fluid from a first fluid supply source through the elongate shaft to the treatment site, a cooling pump configured to pump fluid from a second fluid supply source through the cooling channel, and a controller configured to control the inflow pump and the cooling pump.

20 Claims, 5 Drawing Sheets

(52) U.S. Cl.
CPC .............. *A61B 2018/2253* (2017.05); *A61B 2562/0247* (2013.01)

(58) Field of Classification Search
USPC .............................................. 607/88, 89, 92
See application file for complete search history.

(56) References Cited

U.S. PATENT DOCUMENTS

| | | | |
|---|---|---|---|
| 4,994,026 A | 2/1991 | Fecondini | |
| 5,180,896 A | 1/1993 | Gibby et al. | |
| 5,381,510 A | 1/1995 | Ford et al. | |
| 5,403,277 A | 4/1995 | Dodge et al. | |
| 5,437,629 A | 8/1995 | Goldrath | |
| 5,460,490 A | 10/1995 | Carr et al. | |
| 5,464,391 A | 11/1995 | Vale | |
| 5,520,638 A | 5/1996 | O'Quinn et al. | |
| 5,522,805 A | 6/1996 | Vancaillie et al. | |
| 5,571,389 A | 11/1996 | Kerampran | |
| 5,630,798 A | 5/1997 | Beiser et al. | |
| 5,643,203 A | 7/1997 | Beiser et al. | |
| 5,662,611 A | 9/1997 | Beiser et al. | |
| 5,733,263 A | 3/1998 | Wheatman | |
| 5,810,770 A | 9/1998 | Chin et al. | |
| 5,814,009 A | 9/1998 | Wheatman | |
| 5,875,282 A | 2/1999 | Jordan et al. | |
| 5,919,218 A | 7/1999 | Carr | |
| 5,960,160 A | 9/1999 | Clark et al. | |
| 6,024,720 A | 2/2000 | Chandler et al. | |
| 6,046,442 A | 4/2000 | Kawamura et al. | |
| 6,077,246 A | 6/2000 | Kullas et al. | |
| 6,106,494 A | 8/2000 | Saravia et al. | |
| 6,142,974 A | 11/2000 | Kistner et al. | |
| 6,146,359 A | 11/2000 | Carr et al. | |
| 6,159,160 A | 12/2000 | Hsei et al. | |
| 6,186,752 B1 | 2/2001 | Deniega et al. | |
| 6,238,366 B1 | 5/2001 | Savage et al. | |
| 6,261,261 B1 | 7/2001 | Gordon | |
| 6,293,926 B1 | 9/2001 | Sorensen et al. | |
| 6,302,864 B1 | 10/2001 | Nowosielski | |
| 6,319,221 B1 | 11/2001 | Savage et al. | |
| 6,438,305 B1 | 8/2002 | Kataoka et al. | |
| 6,512,212 B1 | 1/2003 | Leverne Harris | |
| 6,554,791 B1 | 4/2003 | Cartledge et al. | |
| 6,602,221 B1 | 8/2003 | Saravia et al. | |
| 6,699,184 B2 | 3/2004 | Felix et al. | |
| 6,746,439 B2 | 6/2004 | Lenker | |
| 6,775,473 B2 | 8/2004 | Augustine et al. | |
| 6,824,528 B1 | 11/2004 | Faries, Jr. et al. | |
| 6,843,099 B2 | 1/2005 | Derek et al. | |
| 6,896,664 B2 | 5/2005 | Novak | |
| 7,207,966 B2 | 4/2007 | Savare et al. | |
| 7,981,073 B2 | 7/2011 | Möllstam et al. | |
| 8,425,500 B2 | 4/2013 | Hanley et al. | |
| 8,444,592 B2 | 5/2013 | Williams et al. | |
| 8,597,228 B2 | 12/2013 | Pyles et al. | |
| 8,790,303 B2 | 7/2014 | Williams et al. | |
| 8,911,363 B2 | 12/2014 | Kumar et al. | |
| 9,272,086 B2 | 3/2016 | Williams et al. | |
| 9,474,848 B2 | 10/2016 | Williams et al. | |
| 9,492,071 B2 | 11/2016 | Woolford et al. | |
| 9,770,541 B2 | 9/2017 | Carr et al. | |
| 9,907,901 B2 | 3/2018 | Orczy-Timko et al. | |
| 9,962,472 B2 | 5/2018 | Woolford et al. | |
| 9,980,776 B2 | 5/2018 | Peng et al. | |
| 10,016,560 B2 | 7/2018 | Grim et al. | |
| 10,077,767 B2 | 9/2018 | Macari et al. | |
| 10,178,942 B2 | 1/2019 | Germain et al. | |
| 11,850,396 B2 * | 12/2023 | Byrne | A61B 1/00045 |
| 2003/0004470 A1 | 1/2003 | Hickerson et al. | |
| 2003/0216689 A1 | 11/2003 | Bouhuijs et al. | |
| 2004/0030369 A1 * | 2/2004 | Kubota | A61N 5/06 607/89 |
| 2004/0170409 A1 | 9/2004 | Faries, Jr. et al. | |
| 2007/0265689 A1 | 11/2007 | Frey | |
| 2007/0270788 A1 | 11/2007 | Nahen et al. | |
| 2008/0091071 A1 | 4/2008 | Kumar et al. | |
| 2012/0172856 A1 | 7/2012 | Nahen | |
| 2013/0079702 A1 | 3/2013 | Klein et al. | |
| 2017/0184088 A1 | 6/2017 | Macari et al. | |
| 2017/0367749 A1 * | 12/2017 | Gelfand | A61B 18/0218 |
| 2018/0361055 A1 | 12/2018 | Pereira et al. | |
| 2019/0099539 A1 | 4/2019 | Los | |
| 2019/0120223 A1 | 4/2019 | Macari et al. | |
| 2019/0143010 A1 | 5/2019 | Gaspredes et al. | |
| 2019/0290360 A1 * | 9/2019 | Goodrich | A61N 5/062 |
| 2019/0328955 A1 | 10/2019 | Norman et al. | |
| 2019/0388133 A1 | 12/2019 | Sharma | |
| 2020/0352648 A1 | 11/2020 | Tamura et al. | |
| 2020/0405955 A1 * | 12/2020 | Shah | A61B 1/00097 |
| 2021/0085390 A1 * | 3/2021 | Kadamus | A61B 18/04 |
| 2022/0008035 A1 * | 1/2022 | Sartor | A61B 18/22 |
| 2022/0369919 A1 * | 11/2022 | Chu | A61B 1/307 |
| 2023/0083639 A1 * | 3/2023 | Caplan | A61B 1/000094 600/300 |
| 2024/0066219 A1 * | 2/2024 | Byrne | A61M 5/168 |

FOREIGN PATENT DOCUMENTS

| | | |
|---|---|---|
| JP | 2003010207 A | 1/2003 |
| JP | 2005287672 A | 10/2005 |
| JP | 2005312944 A | 11/2005 |
| JP | 2010158531 A | 7/2010 |
| JP | 2020501718 A | 1/2020 |
| WO | 8700759 A1 | 2/1987 |
| WO | 9217040 A1 | 10/1992 |
| WO | 9322979 A1 | 11/1993 |
| WO | 9640331 A1 | 12/1996 |
| WO | 9716220 A1 | 5/1997 |
| WO | 9746271 A1 | 12/1997 |
| WO | WO-2018112261 A1 * 6/2018 ......... A61B 17/3415 |
| WO | 2018236513 A1 | 12/2018 |
| WO | 2019151298 A1 | 8/2019 |

* cited by examiner

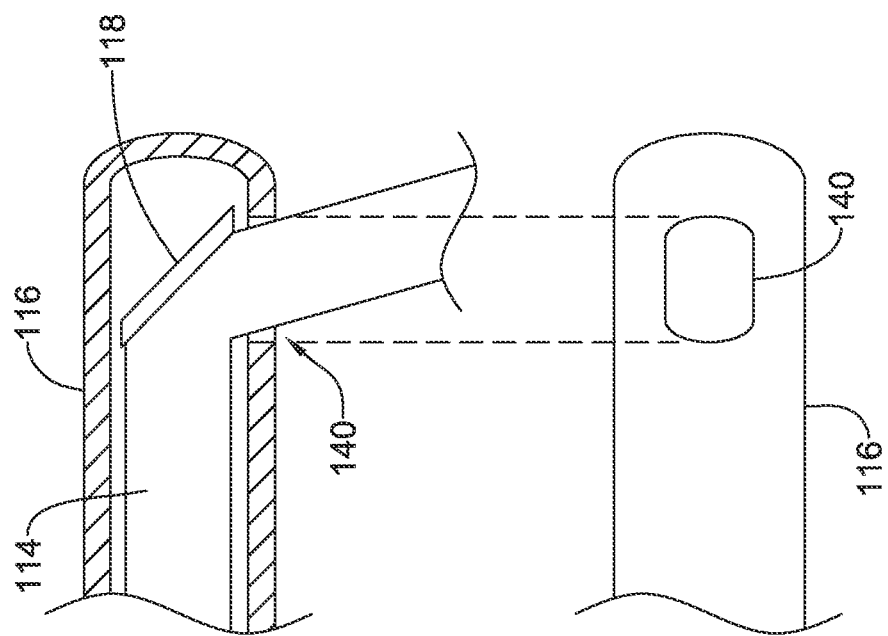

FLUID MANAGEMENT SYSTEM WITH INTEGRATED LASER FIBER COOLING

CROSS REFERENCE TO RELATED APPLICATIONS

This application claims the benefit of and priority to U.S. Provisional Patent Application Ser. No. 63/058,687 filed on Jul. 30, 2020, the disclosure of which is incorporated herein by reference.

TECHNICAL FIELD

The disclosure is directed to a fluid management system. More particularly, the disclosure is directed to a system and method for cooling a laser fiber with a fluid management system.

BACKGROUND

Flexible ureteroscopy (fURS), gynecology, and other endoscopic procedures require the circulation of fluid for several reasons. Surgeons today deliver the fluid in various ways such as, for example, by hanging a fluid bag and using gravity to deliver the fluid, filling a syringe and manually injecting the fluid or using a peristaltic pump to deliver fluid from a reservoir at a fixed pressure or flow rate via a fluid management system. Fluid management systems may adjust the flow rate and/or pressure at which fluid is delivered from the reservoir based on data collected from a procedural device, such as, but not limited to, an endoscope. Of the known medical devices, systems, and methods, each has certain advantages and disadvantages. There is an ongoing need to provide alternative medical devices and fluid delivery systems.

SUMMARY

In a first example, a medical system may comprise: a medical device comprising an elongate shaft configured to access a treatment site within a patient, and a handle coupled to a proximal end of the elongate shaft; a laser device including an elongate tubular member configured for insertion through a working lumen of the medical device, the elongate tubular member including a cooling channel and a laser fiber extending distally within the cooling channel; and a fluid management system comprising an inflow pump configured to pump fluid from a first fluid supply source through the elongate shaft to the treatment site, a cooling pump configured to pump fluid from a second fluid supply source through the cooling channel, and a controller configured to control the inflow pump and the cooling pump.

In addition or alternatively to any example disclosed herein, the cooling pump is a peristaltic pump.

In addition or alternatively to any example disclosed herein, the cooling pump is a diaphragm pump.

In addition or alternatively to any example disclosed herein, the cooling pump is a positive displacement pump.

In addition or alternatively to any example disclosed herein, the cooling pump includes a disposable, single-use pump head.

In addition or alternatively to any example disclosed herein, the fluid management system includes a pressure sensor disposed between the cooling pump and a distal end of the cooling channel.

In addition or alternatively to any example disclosed herein, the fluid management system includes a pressure sensor disposed between the second fluid supply source and the cooling pump.

In addition or alternatively to any example disclosed herein, the cooling pump is configured to pump fluid through the cooling channel at a fluid flow rate between 0 mL/minute and 100 mL/minute.

In addition or alternatively to any example disclosed herein, the cooling pump is configured to pump fluid through the cooling channel at a fluid pressure between 0 mmHg and 500 mmHg.

In addition or alternatively to any example disclosed herein, and in a second example, a medical system may comprise: a medical device comprising an elongate shaft configured to access a treatment site within a patient, and a handle coupled to a proximal end of the elongate shaft; a laser device including an elongate tubular member configured for insertion through a working lumen of the medical device, the elongate tubular member including a cooling channel and a laser fiber extending distally within the cooling channel; and a fluid management system comprising an inflow pump configured to pump fluid from a first fluid supply source through the elongate shaft to the treatment site, a cooling pump configured to pump fluid from a second fluid supply source through the cooling channel, and a controller configured to control the inflow pump and the cooling pump. The laser device may include a laser controller in electronic communication with the controller of the fluid management system.

In addition or alternatively to any example disclosed herein, when the laser controller increases laser power, the controller of the fluid management system speeds up the cooling pump.

In addition or alternatively to any example disclosed herein, when the laser controller terminates laser power, the controller of the fluid management system shuts down the cooling pump.

In addition or alternatively to any example disclosed herein, the laser controller delays activation of laser power until after the controller of the fluid management system activates the cooling pump.

In addition or alternatively to any example disclosed herein, the laser controller monitors a temperature of a distal end of the laser fiber and instructs the controller of the fluid management system to increase cooling pump speed if the temperature exceeds a predetermined limit.

In addition or alternatively to any example disclosed herein, and in a third example, a medical system may comprise: a medical device comprising an elongate shaft configured to access a treatment site within a patient, and a handle coupled to a proximal end of the elongate shaft; a laser device including an elongate tubular member configured for insertion through a working lumen of the medical device, the elongate tubular member including a cooling channel and a laser fiber extending distally within the cooling channel such that the cooling channel surrounds the laser fiber; and a fluid management system comprising an inflow pump configured to pump fluid from a first fluid supply source through the elongate shaft to the treatment site, a cooling pump configured to pump fluid from a second fluid supply source through the cooling channel, and a controller configured to control the inflow pump and the cooling pump. The laser device may include a laser controller in electronic communication with the controller of the fluid management system.

In addition or alternatively to any example disclosed herein, the cooling channel terminates at a distal port proximal a distal end of the elongate tubular member.

In addition or alternatively to any example disclosed herein, laser energy exits the elongate tubular member through the distal port.

In addition or alternatively to any example disclosed herein, the laser device includes a handle portion at a proximal end of the elongate tubular member, the handle portion being configured to rotate the elongate tubular member.

In addition or alternatively to any example disclosed herein, the controller of the fluid management system is configured to control the cooling pump to maintain a target fluid flow rate through the cooling channel based on a set of system operating parameters.

In addition or alternatively to any example disclosed herein, the controller of the fluid management system is configured to control the cooling pump to maintain a target fluid pressure through the cooling channel based on a set of system operating parameters.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The invention may be more completely understood in consideration of the following detailed description in connection with the accompanying drawings, in which:

FIG. 5 illustrates selected aspects of the laser ablation system of FIG. 3.

Figure 1:
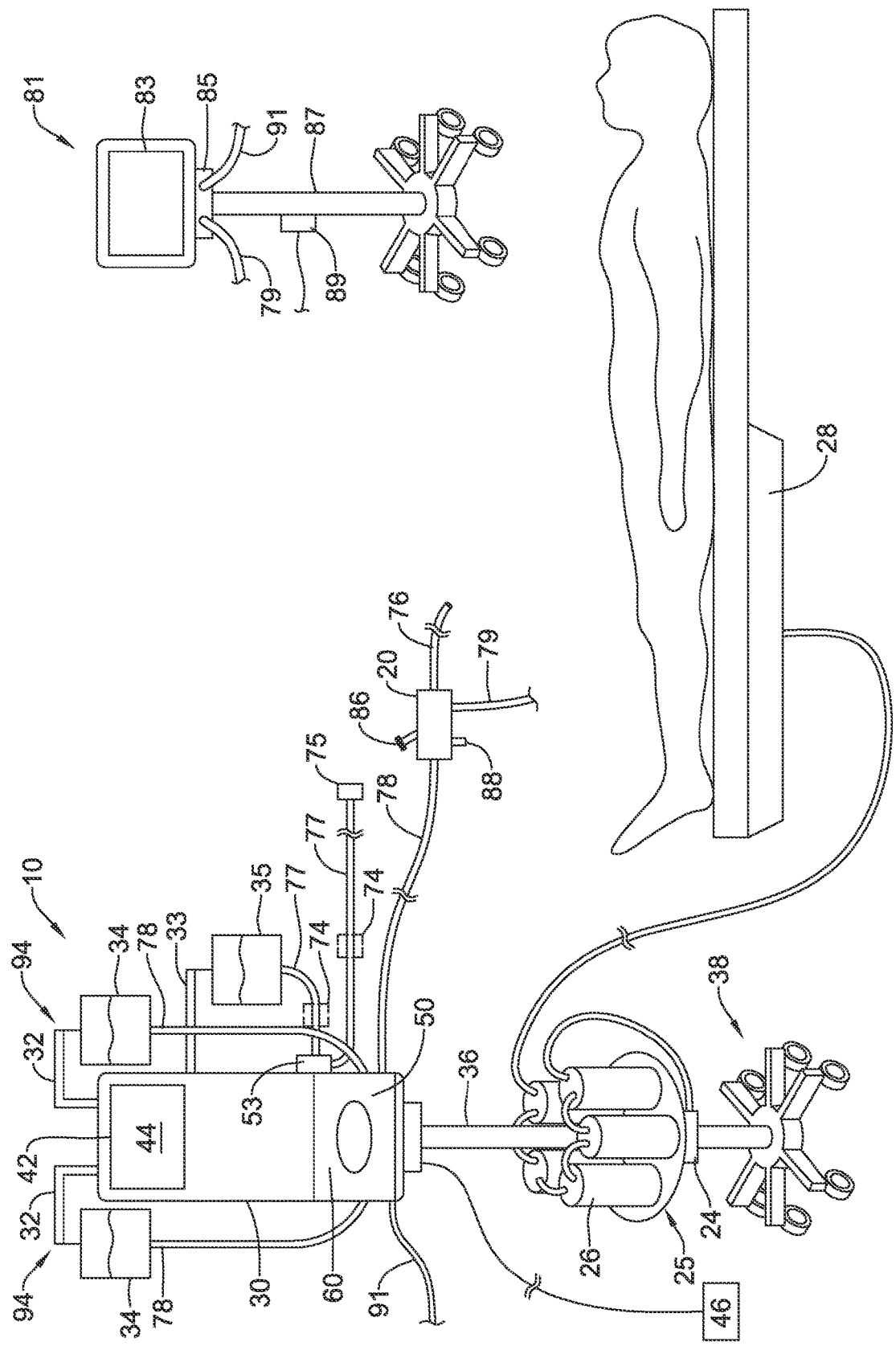
FIG. 1 is a schematic illustration of selected aspects of a fluid management system.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device.

The term "extent" may be understood to mean a greatest measurement of a stated or identified dimension, unless the extent or dimension in question is preceded by or identified as a "minimum", which may be understood to mean a smallest measurement of the stated or identified dimension. For example, "outer extent" may be understood to mean an outer dimension, "radial extent" may be understood to mean a radial dimension, "longitudinal extent" may be understood to mean a longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage, while a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Some fluid management systems for use in flexible ureteroscopy (fURS) procedures (e.g., ureteroscopy, percutaneous nephrolithotomy (PCNL), benign prostatic hyperplasia (BPH), transurethral resection of the prostate (TURP), etc.), gynecology, and other endoscopic procedures may regulate body cavity pressure when used in conjunction with an endoscope device such as, but not limited to, a LithoVue' scope device using pressure and/or temperature data from the endoscope or other endoscopic device. Direct regulation of the intracavity pressure during a medical procedure may allow the fluid management system to safely drive system pressures of up to 600 mmHg to ensure no loss of flow during the procedure when tools are inserted into the working channel of the endoscope device. Fluid deficit may be a concern for physicians, for example during lengthy and/or heavy fluid usage procedures. Excess fluid absorption by the patient may cause serious complications such as edema/water intoxication and/or sepsis condition, for example during BPH/TURP at high pressure and/or in high volume cases. An acceptable loss of fluid (e.g., fluid deficit) may be difficult to determine as it may vary from patient to patient and procedure to procedure. Additionally, keep track of the amount of fluid infused may be difficult as numerous fluid supply sources (e.g., bags of saline, glycine, etc.) may be used during a procedure. Fluid deficit may also be difficult to calculate due to its dependence on the waste collection system, because fluid lost outside of the collection system (e.g., on the floor, for example) may escape inclusion in the calculation. As a result, in some procedures, the fluid deficit is estimated and may be inaccurate. Systems and methods that automate and/or improve the accuracy of fluid deficit calculation and/or monitoring are desired.

FIG. 1 is a schematic view of a fluid management system 10 that may be used in an endoscopic procedure, such as fURS procedures. The fluid management system 10 may be coupled to a medical device 20 that allows flow of fluid therethrough and includes a pressure sensor. An illustrative medical device 20 may be a LithoVue™ scope device, or other endoscope. In an illustrative embodiment, the medical device 20 may include a temperature sensor to provide intracavity temperature feedback to the fluid management system 10, a pressure sensor to provide intracavity pressure feedback to the fluid management system 10, and/or a camera to provide visual feedback to the fluid management system 10.

The fluid management system 10 may include an inflow pump 50 configured to pump and/or transfer fluid from a first fluid supply source 34 (e.g., a fluid bag, etc.) to the medical device 20 and/or the treatment site. In some embodiments, the first fluid supply source 34 may include a plurality of first fluid supply sources (e.g., a plurality of fluid bags). In some cases, the fluid may pass through a fluid warming system 60 prior to entering the medical device 20. The flow of fluid, pressure of the fluid, temperature of the fluid, and other operational parameters may be controlled by or at least partially controlled by a controller 30. The controller 30 may be in electronic communication (e.g., wired or wireless) with the medical device 20, the inflow pump 50, and/or the fluid warming system 60 to provide control commands and/or to transfer or receive data therebetween. For example, the controller 30 may receive data from the medical device 20, such as, but not limited to, pressure and temperature data. In some embodiments, the controller 30 may then use the data received from the medical device 20 to control operational parameters of the inflow pump 50 and/or the fluid warming system 60. In some embodiments, the controller may be configured to control the inflow pump 50 to maintain a target fluid flow rate or target fluid pressure based on a set of system operating parameters. In some embodiments, the controller 30 may be configured to control the inflow pump 50 to maintain a desired fluid pressure at the treatment site or a desired flow rate based on a set of system operating parameters.

The fluid management system 10 also includes a fluid management unit. An illustrative fluid management unit may include one or more fluid container supports, such as fluid supply source hanger(s) 32, each of which supports the first fluid supply source(s) 34. In some embodiments, placement and/or weight of the first fluid supply source(s) 34 may be detected using a remote sensor and/or a supply load cell 94 associated with and/or operatively coupled to each fluid supply source hanger 32 and/or fluid container support. The controller 30 may be in electronic communication with the supply load cell 94. The fluid supply source hanger(s) 32 may be configured to receive a variety of sizes of the first fluid supply source(s) 34 such as, for example, 1 liter (L) to 5 L fluid bags. It will be understood that any number of fluid supply sources 34 may be used. Furthermore, first fluid supply source(s) 34 of any size may be used depending on the procedure. In some embodiments, the fluid management unit may be mounted to a rolling stand, which may include a pole 36 and/or a base 38. The base 38 may include a plurality of wheels to facilitate easy movement of the fluid management unit when in use. However, it will be understood that the first fluid supply source 34 may also be hung from the ceiling or other location depending on the clinical preference. The fluid supply source hanger(s) 32 may extend from the pole 36 and/or the controller 30 and may include one or more hooks from which one or more fluid supply sources 34 may be suspended. In some embodiments, the fluid used in the fluid management unit may be 0.9% saline. However, it will be understood that a variety of other fluids of varying viscosities may be used depending on the procedure.

In some embodiments, the fluid management unit may include a vacuum pump 24 and a collection container 26 in fluid communication with a collection drape 28. In some embodiments, the vacuum pump 24 may include a plurality of vacuum pumps. In some embodiments, the collection container 26 may include a plurality of containers, canisters, and/or other receptacles, which may be fluidly connected to each other and/or the vacuum pump 24. In some embodiments, the collection drape 28 may include a plurality of collection drapes. The vacuum pump 24 may be operatively and/or electronically connected to the controller 30. In some embodiments, the vacuum pump 24 may be disposed adjacent to and/or near the collection container 26, as illustrated in FIG. 1. In some embodiments, the vacuum pump 24 may be disposed within the fluid management system 10. Other configurations are also contemplated. In some embodiments, the collection container 26 may be operatively coupled to a collection load cell 25 to detect placement and/or weight of the collection container 26. In embodiments having a plurality of containers, canisters, and/or other receptacles, each container, canister, and/or receptacle may be operatively coupled to a corresponding collection load cell 25. The controller 30 may be in electronic communication with the collection load cell(s) 25.

The fluid management system 10 may also include one or more user interface components such as a touch screen interface 42. The touch screen interface 42 includes a display screen 44 and may include switches or knobs in addition to touch capabilities. In some embodiments, the controller 30 may include the touch screen interface 42 and/or the display screen 44. The touch screen interface 42 allows the user to input/adjust various functions of the fluid management system 10 such as, for example flow rate, pressure, or temperature. The user may also configure parameters and alarms (such as, but not limited to, a max pressure alarm), information to be displayed, and the procedure mode. The touch screen interface 42 allows the user to add, change, and/or discontinue the use of various modular systems within the fluid management system 10. The touch screen interface 42 may also be used to change the fluid management system 10 between automatic and manual modes for various procedures. It is contemplated that other systems configured to receive user input may be used in place of or in addition to the touch screen interface 42 such as, but not limited to, voice commands.

The touch screen interface 42 may be configured to include selectable areas like buttons and/or may provide a functionality similar to physical buttons as would be understood by those skilled in the art. The display screen 44 may be configured to show icons related to modular systems and devices included in the fluid management system 10. The display screen 44 may also include a flow rate display. In some embodiments, operating parameters may be adjusted by touching a corresponding portion of the touch screen interface 42. The touch screen interface 42 may also display visual alerts and/or audio alarms if parameters (e.g., flow rate, temperature, etc.) are above or below predetermined thresholds and/or ranges. In some embodiments, the fluid management system 10 may also include further user interface components such as an optional foot pedal 46, a heater user interface, a fluid control interface, or other device to manually control various modular systems. For example, the optional foot pedal 46 may be used to manually control flow rate. Some illustrative display screens 44 and other user interface components are described in described in commonly assigned U.S. Patent Application Publication No. 2018/0361055, titled AUTOMATED FLUID MANAGEMENT SYSTEM, the entire disclosure of which is hereby incorporated by reference.

The touch screen interface 42 may be operatively connected to or a part of the controller 30. The controller 30 may be a computer, tablet computer, or other processing device. The controller 30 may be operatively connected to one or more system components such as, for example, the inflow pump 50, the fluid warming system 60, and a fluid deficit management system. In some embodiments, these features may be integrated into a single unit. The controller 30 is capable of and configured to perform various functions such as calculation, control, computation, display, etc. The controller 30 is also capable of tracking and storing data pertaining to the operations of the fluid management system 10 and each component thereof. In some embodiments, the controller 30 may include wired and/or wireless network communication capabilities, such as ethernet or Wi-Fi, through which the controller 30 may be connected to, for example, a local area network. The controller 30 may also receive signals from one or more of the sensors of the fluid management system 10. In some embodiments, the controller 30 may communicate with databases for best practice suggestions and the maintenance of patient records which may be displayed to the user on the display screen 44.

The fluid management system 10 may be user selectable between different modes based on the procedure, patient characteristics, etc. For example, different modes may include, but are not limited to, fURS Mode, BPH Mode, Hysteroscopy Mode, Cystoscopy Mode, etc. Once a mode has been selected by the user, mode parameters such as fluid flow rate, fluid pressure, fluid deficit, and temperature may be provided to the user via the display screen. The exemplary parameters of the specific modes may be previously determined and loaded onto the controller 30 using, for example, software. Thus, when a user selects a procedure from an initial display on the touch screen interface display screen 44, these known parameters may be loaded from the controller 30 to the various components of the fluid management system 10. The fluid management system 10 may also be user selectable between automatic and manual mode. For example, for certain procedures, the user may wish to manually adjust a fluid flow rate, fluid pressure, and/or other parameters. Once the user has selected the manual mode on, for example, the touch screen interface 42, the user may the adjust fluid flow rate or fluid pressure via other manual interfaces such as the optional foot pedal 46, voice commands, or the fluid control interface. If the user selects an automatic mode, the user may be prompted to select or input via the touch screen interface 42 which medical device 20 is being used so that the controller 30 may determine if data obtained from the medical device 20 can be used to facilitate control of the fluid management system 10. In some embodiments, the fluid management system 10 may be configured to verify the medical device 20 selected is actually being used prior to using the collected data.

The controller 30 may be configured to include visual software/image recognition software that can detect visual noise based on variations in brightness (e.g., light monitoring), contrast, or color pixilation. If the image provided to the controller 30 is determined to be not acceptable, the fluid management system 10 may increase the fluid flow rate or the fluid pressure to flush out debris from the treatment site. The fluid flow rate or the fluid pressure may be increased for a temporary time (e.g., a predetermined time period) or until the field of view is deemed to be sufficiently clear. This temporary increase ensures that the time at which the fluid flow rate or the fluid pressure is increased is limited to ensure that intracavity pressure does not exceed safe limits. Alternatively, the controller 30 may provide a visual alert on the display screen 44 or an audible alert to the physician or nurse that a reduced view has been detected and the user may then adjust the irrigation flow rate manually. In some cases, the physician may create a baseline level for visibility at which he or she prefers to initiate a field clearing flow of fluid and input these parameters into the fluid management system 10 via the touch screen interface 42 prior to the procedure. Once the baseline has been created, the fluid management system 10 may monitor the visual feed for variation in the picture and automatically adjust the fluid flow rate as necessary.

In order to adjust the fluid flow rate or the fluid pressure through the fluid management system 10, the fluid management unit may include one or more pressurization devices such as the inflow pump 50. In some embodiments, the inflow pump 50 may be a peristaltic pump. In some embodiments, the inflow pump 50 may include multiple pumps or more than one pump. The inflow pump 50 may be electrically driven and may receive power from a line source such as a wall outlet, an external or internal electrical storage device such as a disposable or rechargeable battery, and/or an internal power supply. The inflow pump 50 may operate at any desired speed sufficient to deliver fluid at a target pressure such as, for example, 5 mmHg to 50 mmHg, and/or at a target fluid flow rate or a target fluid pressure. As noted herein, the inflow pump 50 may be automatically adjusted based on, for example, pressure and/or temperature readings within the treatment site and/or visual feedback from the medical device 20. The inflow pump 50 may also be manually adjusted via, for example, the optional foot pedal 46, the touch screen interface 42, voice commands, or a separate fluid controller. While not explicitly shown, the fluid controller may be a separate user interface including buttons that allow the user to increase or decrease the inflow pump 50. Alternatively, the fluid controller may be incorporated into the main processing device and receive input via the touch screen interface 42, voice commands, or other means of input. It will be understood that any number of pumps may be used. In some embodiments, the fluid management system 10 may include multiple pumps having different flow capabilities. In some embodiments, a flow meter may be located before and/or after the inflow pump 50.

The fluid flow rate or the fluid pressure of the fluid at any given time may be displayed on the display screen 44 to allow the operating room (OR) visibility for any changes. If the OR personnel notice a change in fluid flow rate or fluid pressure that is either too high or too low, the user may manually adjust the fluid flow rate or the fluid pressure back to a preferred level. This may happen, for example, as physicians insert and remove tools into the working channel of the medical device 20. The fluid management system 10 may also monitor and automatically adjust the fluid flow rate or the fluid pressure based on previously set parameters, as discussed herein. This feature may also be beneficial when fluid flow is provided manually such as an assistant injecting irrigation through a syringe.

In some embodiments, the fluid management system 10 may include visual software or image recognition and analysis software. For example, the fluid management system 10 may detect, such as via a camera positioned on the medical device 20 within the body, whether a tool has been inserted or not and which tool is being used. The tool may, for example, have an identifiable marker that the visual software may see to inform the fluid management system 10 what type of tool is being used. The fluid management system 10 may then automatically adjust the fluid flow rate or the fluid pressure based on the tool identified by the visual software. When the tool is retracted from the working channel, the fluid management system 10 may automatically reduce the fluid flow rate or the fluid pressure accordingly.

Additionally, or alternatively, the fluid management system 10 may automatically adjust the fluid flow rate or the fluid pressure based on an intracavity temperature and/or pressure detected within the treatment site. The intracavity temperature and/or pressure may be measured in situ using a temperature sensor and/or a pressure sensor mounted on the medical device 20, used in conjunction with the fluid management system 10. In some embodiments, the fluid management system 10 may include flow monitoring software so that the inflow pump 50 may be configured by the user to be automatically started, stopped, and/or speed adjusted by the fluid management system 10 to maintain a fluid flow rate delivered to the treatment site at a target flow rate and/or within a predetermined flow rate range. In some embodiments, the fluid management system 10 may include pressure monitoring software so that the inflow pump 50 may be configured by the user to be automatically started, stopped, and/or speed adjusted by the fluid management system 10 to maintain a fluid pressure delivered to the treatment site at a target pressure and/or within a predetermined pressure range. For example, the pressure sensor may detect pressure within the treatment site (for example, a kidney or uterus) and automatically alter the fluid flow rate or the fluid pressure within the fluid management system 10 based on a monitored intracavity (e.g., intrarenal or intrauterine) pressure. If the intracavity pressure is too high, the fluid management system 10 may decrease the fluid flow rate or the fluid pressure and if the intracavity pressure is too low, the fluid management system 10 may increase the fluid flow rate or the fluid pressure. In an exemplary temperature control mode, the fluid management system 10 may include temperature monitoring software so that the fluid warming system 60 may be controlled (e.g., started, stopped, and temperature adjusted) to maintain a fluid temperature delivered to a treatment site at about a target temperature and/or within a predetermined temperature range. For example, the temperature may be monitored in vivo or in vitro and the flow of fluid altered based on the temperature feedback provided. In an illustrative embodiment, the fluid management system 10 may compare the temperature and/or pressure sensed within the treatment site to known values and provide a warning when the parameters are outside of a predetermined safe range. The warning may be a visual or audio alert.

In some embodiments, the medical device 20 may be a ureteroscope such as a LithoVue™ scope. However, other medical devices, such as another endoscope, may be used in addition to or in place of a ureteroscope. The medical device 20 may be configured to deliver fluid from the fluid management system 10 to the treatment site via an elongate shaft 76 configured to access the treatment site within the patient. In some embodiments, the inflow pump 50 may be in fluid communication with the elongate shaft 76. The elongate shaft 76 may include one or more working lumens for receiving a flow of fluid or other medical devices therethrough. The medical device 20 is connected to the fluid management system 10 via one or more supply line(s) 78 (e.g., a tube).

In some embodiments, the medical device 20 may be in electronic communication with a workstation 81 via a wired connection 79. The workstation 81 may include a touch panel computer 83, an interface box 85 for receiving the wired connection 79, a cart 87, and a power supply 89, among other features. In some embodiments, the interface box 85 may be configured with a wired or wireless communication connection 91 with the controller 30 of the fluid management system 10. The touch panel computer 83 may include at least a display screen and an image processor. In some embodiments, the workstation 81 may be a multi-use component (e.g., used for more than one procedure) while the medical device 20 may be a single use device, although this is not required. In some embodiments, the workstation 81 may transmit pressure data (e.g., obtained with the medical device 20) to the controller 30 of the fluid management system 10. The controller 30 of the fluid management system 10 may then use the pressure data from the medical device 20 to adjust fluid flow rates or fluid pressure when a user-specified or predetermined pressure limit is reached. In some embodiments, the workstation 81 may be omitted and the medical device 20 may be electronically coupled directly to the controller 30 of the fluid management system 10.

The one or more supply line(s) 78 from the fluid management system 10 to the medical device 20 may be formed of a material the helps dampen the peristaltic motion created by the inflow pump 50. In some embodiments, the medical device 20 may include one or more sensors proximate a distal end of the elongate shaft 76. For example, the medical device 20 may include a pressure sensor at a distal tip of the elongate shaft 76 to measure intracavity pressure within the treatment site. The medical device 20 may also include other sensors such as, for example, a temperature sensor, a Fiber Bragg grating optical fiber to detect stresses, and/or an antenna or electromagnetic sensor (e.g., a position sensor). In some embodiments, the distal end of the medical device 20 may also include at least one camera to provide a visual feed to the user on the display screen of the touch panel computer 83. In some embodiments, the medical device 20 may include two cameras having different communications requirements or protocols so that different information may be relayed to the user by each camera. When so provided, the user may switch back and forth between cameras at will through the touch screen interface 42 and/or the touch panel computer 83. In some embodiments, the one or more sensors may be used to verify that the medical device 20 is actually in use and/or is positioned within the patient. While not explicitly shown, the medical device 20 and/or the elongate shaft 76 may include one or more working lumens for receiving the fluid and/or other medical devices.

The medical device 20 includes a handle coupled to a proximal end of the elongate shaft 76. The handle may have a fluid flow on/off switch, which allows the user to control when fluid is flowing through the medical device 20 and into the treatment site. The handle may further include other buttons that perform other various functions. For example, in some embodiments, the handle may include buttons to control the temperature of the fluid. In some embodiments, the medical device 20 may include a laser so that the user may fire laser energy. A laser fiber may be connected to the laser system and inserted through a working lumen of the medical device 20. The user may fire the laser so that energy comes out of the tip of the laser fiber and hits the debris/stone to break it up and/or ablates targeted tissue. In some embodiments including a laser, a communication line between the laser system and the handle of the medical device 20 is maintained (e.g., hardwire or wireless). It will be understood that while the exemplary embodiment describes a ureteroscope, the features detailed above may also be directly integrated into a cystoscope, an endoscope, a hysteroscope, or virtually any device with an image capability. In some embodiments, the medical device 20 may also include a drainage port 88 which may be connected to a drainage system. Some illustrative drainage systems are described in commonly assigned U.S. Patent Application Publication No. 2018/0361055, titled AUTOMATED FLUID MANAGEMENT SYSTEM, the disclosure of which is hereby incorporated by reference.

In some embodiments, the controller 30 may be configured to calculate a fluid deficit when the distal end of the elongate shaft 76 is disposed within the patient, the fluid deficit being representative of fluid lost, absorbed by the patient, and/or otherwise unaccounted for during a procedure.

Prior to starting the procedure, the fluid management system 10 may need to be primed to remove any air from the system. Priming the fluid management system 10 may result in some fluid being lost. In some embodiments, the controller 30 may be configured to automatically reset the fluid deficit to zero after priming of the fluid management system 10. In some embodiments, the controller 30 may be configured to automatically begin fluid deficit calculation when signals from the one or more sensors indicate the distal end of the elongate shaft 76 is inserted within the patient. In some embodiments, the controller 30 may be configured to automatically pause fluid deficit calculation when the distal end of the elongate shaft 76 is removed from the patient. In some embodiments, the controller 30 may be configured to automatically resume fluid deficit calculation when signals from the one or more sensors indicate the distal end of the elongate shaft 76 is reinserted into the patient. In some embodiments, the controller 30 may be configured to calculate the fluid deficit only when the distal end of the elongate shaft 76 is disposed within the patient.

In some embodiments, fluid deficit calculation may begin after initial set-up of the system (e.g., prior to priming). In some embodiments, fluid used during priming of the system may be excluded from the fluid deficit calculation and/or may be subtracted from the calculated fluid deficit to determine a true fluid deficit. For example, the supply line(s) 78 and/or the heater cassette 64 may define and/or contain a known fluid volume. In some embodiments, the controller 30 may be configured to exclude the known fluid volume of the supply line(s) 78 and/or the heater cassette 64 from the fluid deficit calculation.

In some embodiments, the controller 30 may be configured to notify a user when the total fluid deficit reaches a preset fluid deficit limit. In some embodiments, the controller 30 may be configured to stop the inflow pump 50 and/or the vacuum pump 24 when the total fluid deficit reaches the preset fluid deficit limit.

In some embodiments, the controller 30 may be configured to notify a user when a total amount of fluid infused reaches a preset fluid infusion limit. In some embodiments, the controller 30 may be configured to stop the inflow pump 50 and/or the vacuum pump 24 when the total amount of fluid infused reaches the preset fluid infusion limit.

In some embodiments, the controller 30 may be configured to monitor the amount of fluid in the first fluid supply source 34 through weight using, for example, the supply load cell 94, a scale, or other suitable means. The readout of the supply load cell 94 may be shown to the user on the display screen 44. As the procedure proceeds, the readout of the supply load cell 94 may be updated in real time to alert the physician to how much fluid is left in the first fluid supply source 34 and this amount may then be used to determine how much fluid has been infused into the patient. In some embodiments, the amount of fluid remaining and/or an amount of time (e.g., at the current usage rate) fluid will remain in the first fluid supply source 34 may be shown. An alert may be shown on the display screen 44 with an audible signal when, for example, 10% of the fluid is left in the first fluid supply source 34. In some embodiments, the supply load cell 94 may connect to the display screen 44 via a wireless (e.g., Wi-Fi) signal. In some embodiments, the supply load cell 94 may be connected to the display screen 44 via a hard wire connection.

Similarly, the controller 30 may be configured to monitor the amount of fluid in the collection container 26 through weight using, for example, the collection load cell 25, a scale, or other suitable means. The readout of the collection load cell 25 may be shown to the user on the display screen 44. As the procedure proceeds, the readout of the collection load cell 25 may be updated in real time to alert the physician to how much fluid is in the collection container 26 and this amount may then be used to determine how much fluid has been collected from the patient and/or the collection drape 28. In some embodiments, the amount of fluid in the collection container 26 and/or an amount of time remaining before the collection container 26 is full may be shown. An alert may be shown on the display screen 44 with an audible signal when, for example, 10% of an initial empty volume is left in the collection container 26. In some embodiments, the collection load cell 25 may connect to the display screen 44 via a wireless (e.g., Wi-Fi) signal. In some embodiments, the collection load cell 25 may be connected to the display screen 44 via a hard wire connection.

In some embodiments, the fluid management system 10 may include a pressure sensor connected inline between the first fluid supply source 34 and the medical device 20, wherein pressure within the supply line(s) 78 is determined based on the height of the first fluid supply source 34. The amount of head pressure decreases as the first fluid supply source 34 empties. When the pressure falls below a threshold set by the user, an alert may be shown on the display screen 44 and an audible signal may be emitted. In some embodiments, a flow rate sensor may be connected inline between the first fluid supply source 34 and the medical device 20. The flow rate sensor may be operably connected to the controller 30 and data from the flow rate sensor may be used by the controller 30 to change selected system parameters and/or may be used in fluid deficit calculation(s).

The fluid management system 10 may utilize supply line(s) 78 to connect various components. In some embodiments, the supply line(s) 78 may formed from small diameter tubing less than or equal to ¹⁄₁₆ inches (1.5875 millimeters) in diameter. However, it will be understood that tubing size may vary based on the application. The supply line(s) 78 and/or the tubing may be disposable and provided sterile and ready to use. Different types of tubing may be used for various functions within the fluid management system 10. For example, one type of tubing may be used for fluid heating and fluid flow control to the medical device 20 while another type of tubing may be used for irrigation within the body and/or the treatment site.

Figure 2:
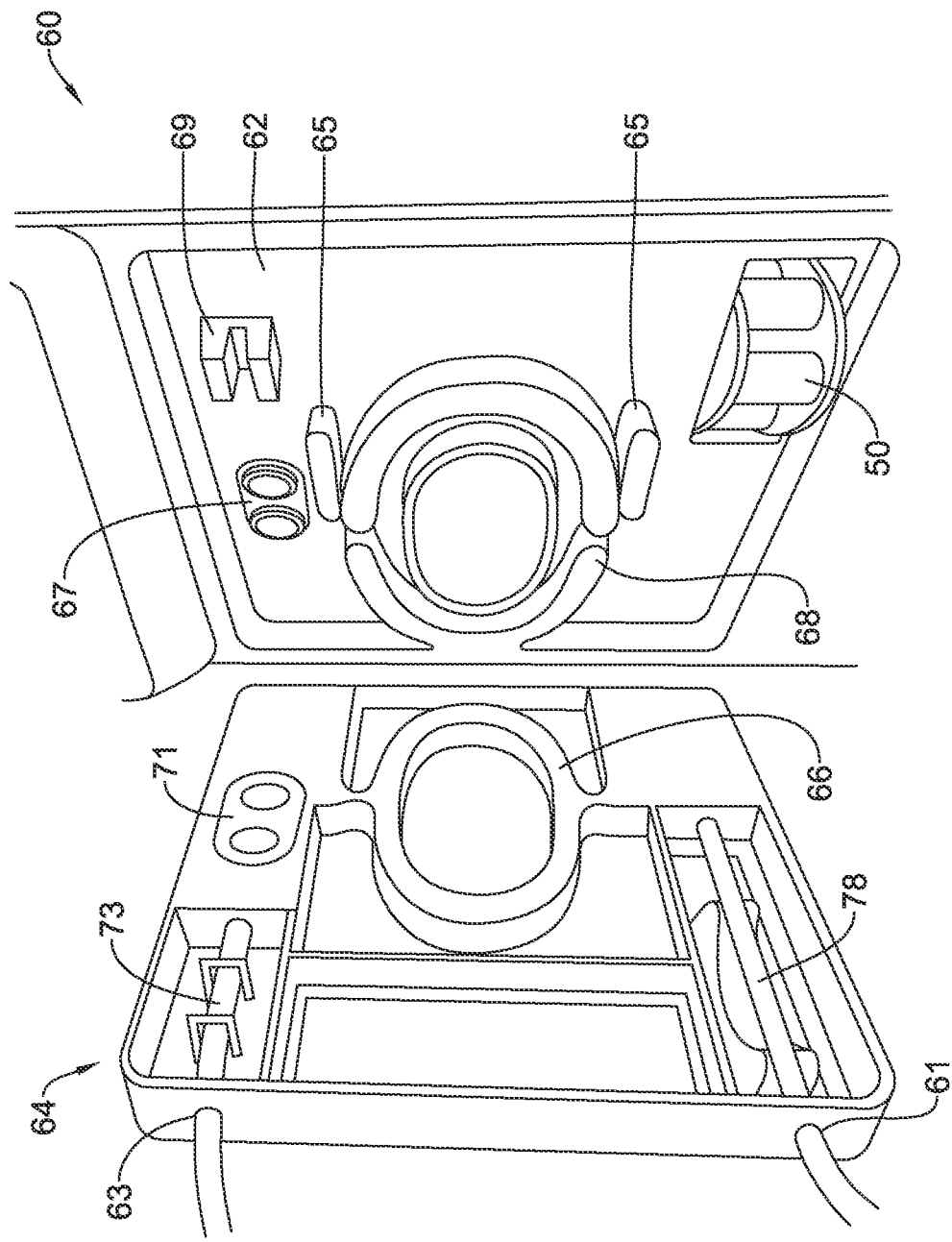
FIG. 2 is a partial perspective view illustrating selected aspects of the fluid management system of FIG. 1.

In some embodiments, the fluid management system 10 may include a fluid warming system 60, as shown in more detail in FIG. 2, for heating fluid to be delivered to the patient. The fluid warming system 60 may include a heater 62 and a heater cassette 64. The heater cassette 64 may be configured to be a single use heater cassette 64 while the heater 62 may be reused for multiple procedures. For example, the heater cassette 64 may isolate fluid flow therein such that the heater 62 may be reused with minimal maintenance. The heater cassette 64 may be formed of, for example, polycarbonate or any high heat rated biocompatible plastic and is formed as a single unitary and/monolithic piece or a plurality of pieces permanently bonded to one another. In some embodiments, the heater cassette 64 may include a fluid inlet port 61 and a fluid outlet port 63 located at a lateral side of the heater cassette 64. The fluid inlet port 61 and the fluid outlet port 63 may each be configured to couple to the supply line(s) 78 of the fluid management system 10. For example, the fluid inlet port 61 may couple the first fluid supply source 34, the inflow pump 50, and the fluid warming system 60 while the fluid outlet port 63 may couple the fluid warming system 60 with the medical device 20, each via the supply line(s) 78. The inflow pump 50 is illustrated in FIG. 2 as a peristaltic pump, but other configurations and/or types of pumps are also contemplated.

In some embodiments, the heater cassette 64 may include an internal flow path along a channel through which fluid may flow from the fluid inlet port 61 to the fluid outlet port 63. The heater cassette 64 may include one fluid path or multiple fluid paths. In some embodiments, the channel may pass through a susceptor 66 which may allow the fluid to be heated via induction heating. When the heater cassette 64 is coupled with the heater 62, the susceptor 66 may be positioned within an induction coil 68 configured to heat the fluid flowing through the susceptor 66. Other fluid warming system configurations and methods may also be used, as desired. For example, the heater 62 may include one or more heat sources such as, for example a platen system or an inline coil in the supply line(s) 78 using electrical energy. Heating may be specifically designed and tailored to the flow rates required in the specific application of the fluid management system 10. Some illustrative fluid warming systems 60 are described in described in commonly assigned U.S. Patent Application Publication No. 2018/0361055, titled AUTOMATED FLUID MANAGEMENT SYSTEM, the entire disclosure of which is hereby incorporated by reference.

While not explicitly shown, the fluid warming system 60 may include a heater user interface separate from the touch screen interface 42. In one example, the heater user interface may simply be a display screen providing a digital display of the internal temperature of the heater 62. In another embodiment, the user interface may also include temperature adjustment buttons to increase or decrease the temperature of the heater 62. In this embodiment, the heater user interface and/or the display screen may indicate the current temperature of the heater 62 as well as the target temperature to be reached. It is noted that all information output from the fluid warming system 60 may be transmitted directly to the display screen 44 such that no heater user interface is necessary.

The fluid warming system 60 may include one or more sensors configured to monitor the fluid flowing therethrough. For example, temperature sensors 65 may be mounted in the fluid warming system 60 such that they detect the temperature of the fluid flowing through the heater cassette 64. In some embodiments, the temperature sensors 65 may be located at or near the fluid inlet port 61 and/or the fluid outlet port 63. In some embodiments, the temperature sensors 65 may be mounted so that they detect the temperature of fluid flowing through the heater cassette 64 prior to the fluid entering the susceptor 66 and after fluid exits the susceptor 66. In some embodiments, additional sensors may be located at a medial portion of the susceptor 66 so that they detect a progression of temperature increase of the fluid in the heater cassette 64. The temperature sensors 65 may remotely send any information to the display screen 44 or they may send information to heater user interface and/or the display screen thereof, if so provided. In another embodiment, the temperature sensors 65 may be hardwired with the heater user interface (if provided) which is then able to remotely transmit desired information to the display screen 44. Alternatively, or additionally, the temperature sensors 65 may be hardwired to and/or with the controller 30.

The heater 62 may further include a pressure sensor 67 and/or a bubble sensor 69. The heater cassette 64 may include a corresponding pressure sensor interface 71 and bubble sensor interface 73 that allow the pressure sensor 67 and the bubble sensor 69, respectively, to monitor the fluid flowing through the heater cassette 64 when the heater cassette 64 is coupled with the fluid warming system 60. The pressure sensor 67 and/or the bubble sensor 69 may remotely send any information to the display screen 44 or they may send information to the heater user interface and/or the display screen thereof, if so provided. In another embodiment, the pressure sensor 67 and/or the bubble sensor 69 may be hardwired with the heater user interface (if provided) which is then able to remotely transmit desired information to the display screen 44. Alternatively, or additionally, the pressure sensor 67 and/or the bubble sensor 69 may be hardwired to and/or with the controller 30.

Figure 3:
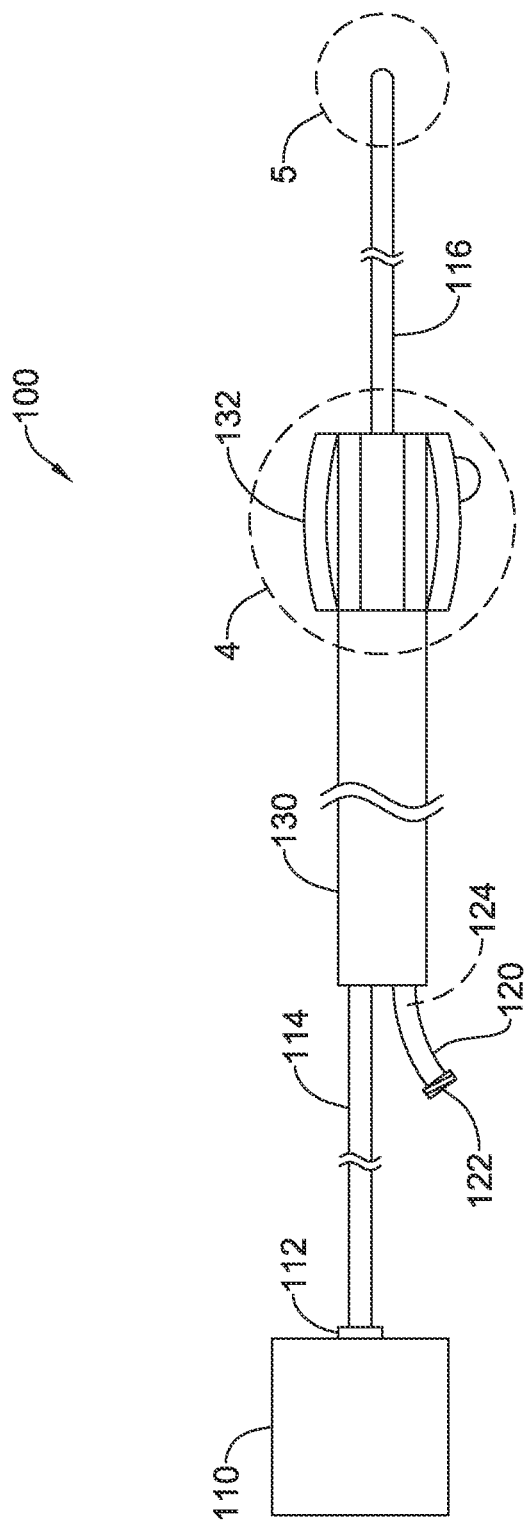
FIG. 3 is a schematic illustration of selected aspects of a laser ablation system.

In some embodiments, a medical system may comprise the medical device 20, as described herein, the fluid management system 10, as described herein, and a laser device 100. FIG. 3 illustrates one exemplary laser device 100 usable with the medical system. In some embodiments, the laser device 100 may include a laser controller 110. In some embodiments, the laser controller 110 may be in electronic communication (e.g., wired or wireless) with the controller 30 of the fluid management system 10. In some embodiments, the laser device 100 may include an elongate tubular member 116 configured for insertion through a working lumen of the medical device 20 and/or the elongate shaft 76 of the medical device 20. The laser device 100 may include a proximal elongate member and/or a laser fiber 114 extending from a proximal connector 112 to a handle portion 130. In some embodiments, the laser fiber 114 may extend and/or be disposed inside of the proximal elongate member to protect the laser fiber 114. The proximal connector 112 may connect the proximal elongate member and/or the laser fiber 114 to the laser controller 110.

The handle portion 130 may be disposed at a proximal end of the elongate tubular member 116 and/or the elongate tubular member 116 may extend distally from the handle portion 130. The laser fiber 114 may extend longitudinally through the handle portion 130 and the elongate tubular member 116 to a position proximate a distal end of the elongate tubular member 116. The laser device 100 and/or the handle portion 130 of the laser device 100 may include a cooling tube 120 extending proximally from a proximal portion and/or a proximal end of the handle portion 130 to a cooling tube connector 122. The cooling tube 120 may define a cooling tube lumen 124 extending from the cooling tube connector 122 into the handle portion 130. In some embodiments, the cooling tube 120 may extend into the handle portion 130. In some embodiments, the handle portion 130 may define a separate segment of the cooling tube lumen 124 within the handle portion 130, wherein the separate segment is in fluid communication with the cooling tube lumen 124.

In some embodiments, the handle portion 130 may include a knob portion 132 proximate a distal end of the handle portion 130. In at least some embodiments, the knob portion 132 of the handle portion 130 and/or the handle portion 130 may be configured to rotate the elongate tubular member 116. In some embodiments, the elongate tubular member 116 may be non-rotatably and/or fixedly attached to the knob portion 132 of the handle portion 130. In some embodiments, the knob portion 132 may be rotatable relative to the handle portion 130 and/or the laser fiber 114 disposed therein and/or extending therethrough. In some embodiments, the knob portion 132 may include a thumb paddle extending radially outward to aid in rotating the knob portion 132.

Figure 4:
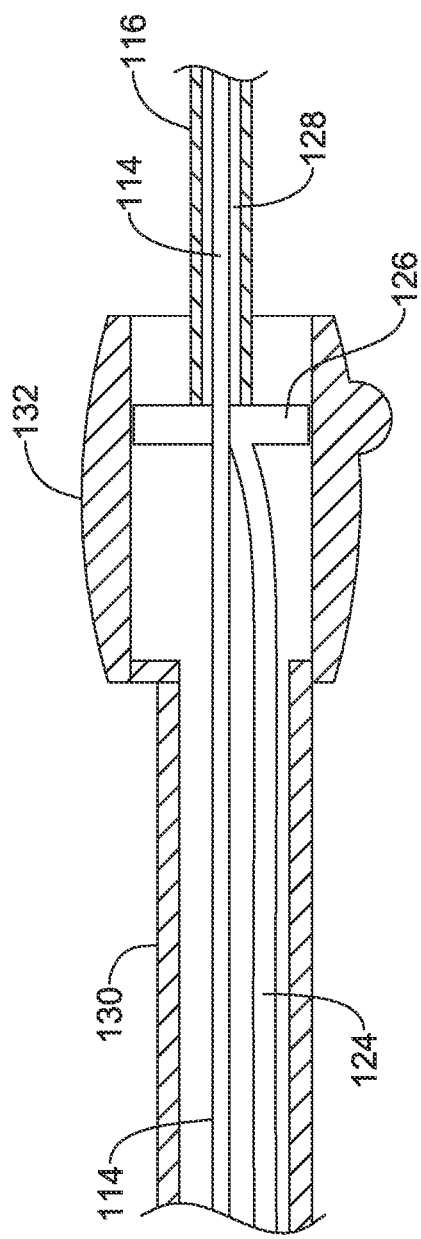
FIG. 4 is a partial cross-section of a portion of the laser ablation system of FIG. 3.

As illustrated in the partial cross-section shown in FIG. 4, the laser fiber 114 may extend through the handle portion 130 and/or the knob portion 132 of the handle portion 130. The cooling tube lumen 124 may extend from the proximal portion and/or the proximal end of the handle portion 130 to a cooling reservoir 126 disposed within the handle portion 130 and/or the knob portion 132 of the handle portion 130. In embodiments, where the handle portion 130 defines a separate segment of the cooling tube lumen 124, the separate segment is in fluid communication with both the cooling tube lumen 124 of the cooling tube 120 and the cooling reservoir 126. The cooling reservoir 126 may substantially surround the laser fiber 114 and/or the laser fiber 114 may extend through the cooling reservoir 126. As also seen in FIG. 4, the elongate tubular member 116 may include a cooling channel 128 and the laser fiber 114 extending distally within the cooling channel 128. The cooling channel 128 may be in fluid communication with the cooling reservoir 126 and/or the cooling tube lumen 124. In some embodiments, the cooling channel 128 may substantially surround the laser fiber 114. In some embodiments, the laser fiber 114 may be coaxially disposed within the cooling channel 128. In some embodiments, the laser fiber 114 may be offset from a central longitudinal axis of the cooling channel 128.

As seen in FIG. 5, the elongate tubular member 116 may include a closed distal tip. FIG. 5 is illustrated with a side view of the elongate tubular member 116 in partial cross-section at the top of the page, and a bottom view of the elongate tubular member 116 at the bottom of the page. The laser device 100 and/or the elongate tubular member 116 may include a mirror 118 disposed within a distal portion of the elongate tubular member 116. The laser fiber 114 may terminate at and/or adjacent to the mirror 118. The mirror 118 may be a reflective element configured to redirect laser energy from the laser fiber 114 out a distal port 140 of the elongate tubular member 116 such that laser energy exits the elongate tubular member 116 through the distal port 140, as shown in FIG. 5. In some embodiments, the cooling channel 128 may terminate at the distal port 140. In some embodiments, fluid flowing through and/or within the cooling channel 128 may exit the elongate tubular member 116 through the distal port 140. In some embodiments, the distal port 140 may be disposed proximal of a distal end and/or the distal tip of the elongate tubular member 116.

A distal end of the laser fiber 114 may become hot as the laser device 100 is used. Too much heat generated may damage the distal end of the laser fiber 114. The cooling channel 128 is used to provide liquid cooling of the laser fiber 114 to improve longevity and function of the laser fiber 114 and/or the laser device 100. However, insufficient flow and/or pressure of fluid over the laser fiber 114 may permit excess heat to build up at the distal end of the laser fiber 114. Laser fibers such as those in the laser device 100 that have used liquid cooling have typically been cooled using a gravity feed system, where the pressure and flow of fluid may vary and/or decrease over time as the fluid source is drained. In order to provide better cooling of the laser fiber 114, alternative fluid management system configuration(s) may be desired.

Returning to FIG. 1, the fluid management system 10 may further include a second fluid supply source 35 and a second fluid supply source hanger 33 mounted to the fluid management unit, wherein the second fluid supply source hanger 33 supports the second fluid supply source 35. In some embodiments, placement and/or weight of the second fluid supply source 35 may be detected using a remote sensor and/or a cooling supply load cell associated with and/or operatively coupled to the second fluid supply source hanger 33. The controller 30 may be in electronic communication with the cooling supply load cell. The second fluid supply source hanger 33 may be configured to receive a variety of sizes of the second fluid supply source 35 such as, for example, 1 liter (L) to 5 L fluid bags. It will be understood that any number of second fluid supply sources 35 may be used. Furthermore, a second fluid supply source 35 of any size may be used depending on the procedure. The second fluid supply source hanger 33 may extend from the pole 36 and/or the controller 30 and may include one or more hooks from which the second fluid supply source 35 may be suspended. In some embodiments, the second fluid supply source 35 may be 0.9% saline. However, it will be understood that a variety of other fluids of varying viscosities may be used depending on the procedure.

The fluid management system 10 may include a cooling pump 53 configured to pump fluid from the second fluid supply source 35 under pressure. In some embodiments, the cooling pump 53 may be a peristaltic pump, a diaphragm pump, a positive displacement pump, or other suitable pump type. In some embodiments, the cooling pump 53 may include a disposable, single-use pump head configured and/or designed to be replaced after each procedure. For example, the cooling pump 53 may be a standalone pump disposed outside of the fluid management unit. In some embodiments, the cooling pump 53 may be mounted to an outside surface and/or may face an exterior of the fluid management unit. In some embodiments, the cooling pump 53 may be reusable. For example, the cooling pump 53 may be disposed within the fluid management unit. In at least some embodiments, the controller 30 of the fluid management unit and/or the fluid management system 10 may be configured to control the inflow pump 50 and the cooling pump 53.

The fluid management system 10 may include one or more cooling supply lines 77. For example, a cooling supply line 77 may connect the second fluid supply source 35 to the cooling pump 53. Additionally, a cooling supply line 77 may extend from the cooling pump 53 to a distal connector 75, such as a luer connector for example, at a distal end of the cooling supply line 77. In some embodiments, depending upon the type of pump that cooling pump 53 is for example, the cooling supply line 77 may extend from the second fluid supply source 35 through the cooling pump 53 to the distal connector 75. In at least some embodiments, the distal connector 75 may be configured to connect to the cooling tube connector 122 of the laser device 100, thereby establishing a fluid pathway from the second fluid supply source 135 to the distal port 140.

In some embodiments, the cooling pump 53 may be configured to pump fluid from the second fluid supply source 35 through the cooling supply line 77, the cooling tube 120, the cooling tube lumen 124, the cooling reservoir 126, and/or the cooling channel 128 under pressure. In some embodiments, the controller 30 of the fluid management system 10 may be configured to control the cooling pump 53 to maintain a target fluid flow rate through the cooling supply line 77, the cooling tube 120, the cooling tube lumen 124, the cooling reservoir 126, and/or the cooling channel 128 based on a set of system operating parameters. In some embodiments, the controller 30 of the fluid management system 10 may be configured to control the cooling pump 53 to maintain a target fluid pressure through the cooling supply line 77, the cooling tube 120, the cooling tube lumen 124, the cooling reservoir 126, and/or the cooling channel 128 based on a set of system operating parameters.

In some embodiments, the cooling pump 53 may be configured to pump fluid from the second fluid supply source 35 through the cooling supply line 77, the cooling tube 120, the cooling tube lumen 124, the cooling reservoir 126, and/or the cooling channel 128 at a fluid flow rate between 0 milliliters (mL)/minute and 100 mL/minute. In some embodiments, the cooling pump 53 may be configured to pump fluid from the second fluid supply source 35 through the cooling supply line 77, the cooling tube 120, the cooling tube lumen 124, the cooling reservoir 126, and/or the cooling channel 128 at a fluid flow rate between 0 milliliters (mL)/minute and 75 mL/minute. In some embodiments, the cooling pump 53 may be configured to pump fluid from the second fluid supply source 35 through the cooling supply line 77, the cooling tube 120, the cooling tube lumen 124, the cooling reservoir 126, and/or the cooling channel 128 at a fluid flow rate between 0 milliliters (mL)/minute and 50 mL/minute. In some embodiments, the cooling pump 53 may be configured to pump fluid from the second fluid supply source 35 through the cooling supply line 77, the cooling tube 120, the cooling tube lumen 124, the cooling reservoir 126, and/or the cooling channel 128 at a fluid flow rate between 0 milliliters (mL)/minute and 25 mL/minute. Other configurations are also contemplated.

In some embodiments, the cooling pump 53 may be configured to pump fluid from the second fluid supply source 35 through the cooling supply line 77, the cooling tube 120, the cooling tube lumen 124, the cooling reservoir 126, and/or the cooling channel 128 at a fluid pressure between 0 millimeters of mercury (mmHg) and 500 mmHg.

In some embodiments, the cooling pump 53 may be configured to pump fluid from the second fluid supply source 35 through the cooling supply line 77, the cooling tube 120, the cooling tube lumen 124, the cooling reservoir 126, and/or the cooling channel 128 at a fluid pressure between 0 and 300 mmHg. In some embodiments, the cooling pump 53 may be configured to pump fluid from the second fluid supply source 35 through the cooling supply line 77, the cooling tube 120, the cooling tube lumen 124, the cooling reservoir 126, and/or the cooling channel 128 at a fluid pressure between 0 millimeters of mercury (mmHg) and 200 mmHg. In some embodiments, the cooling pump 53 may be configured to pump fluid from the second fluid supply source 35 through the cooling supply line 77, the cooling tube 120, the cooling tube lumen 124, the cooling reservoir 126, and/or the cooling channel 128 at a fluid pressure between 0 millimeters of mercury (mmHg) and 100 mmHg. In some embodiments, the cooling pump 53 may be configured to pump fluid from the second fluid supply source 35 through the cooling supply line 77, the cooling tube 120, the cooling tube lumen 124, the cooling reservoir 126, and/or the cooling channel 128 at a fluid pressure between 0 millimeters of mercury (mmHg) and 50 mmHg. In some embodiments, the cooling pump 53 may be configured to pump fluid from the second fluid supply source 35 through the cooling supply line 77, the cooling tube 120, the cooling tube lumen 124, the cooling reservoir 126, and/or the cooling channel 128 at a fluid pressure between 0 millimeters of mercury (mmHg) and 25 mmHg. Other configurations are also contemplated.

In some embodiments, the fluid management system 10 may optionally include a pressure sensor 74 disposed between the second fluid supply source 35 and the cooling pump 53. Such placement may permit, among other uses, detection of a loss of fluid flowing into the cooling pump 53. In some embodiments, the fluid management system 10 may optionally include a pressure sensor 74 disposed between the cooling pump 53 and a distal end of the cooling channel 128. Such placement may permit, among other uses, detection of fluid pressure and/or presence and/or flow of fluid through the cooling supply line 77, the cooling tube 120, the cooling tube lumen 124, the cooling reservoir 126, and/or the cooling channel 128, and/or may prevent over pressurization of the cooling supply line 77, the cooling tube 120, the cooling tube lumen 124, the cooling reservoir 126, and/or the cooling channel 128. In some embodiments, the fluid management system 10 may optionally include a pressure sensor 74 disposed between the second fluid supply source 35 and the cooling pump 53 and another pressure sensor 74 disposed between the cooling pump 53 and a distal end of the cooling channel 128. In some embodiments, the fluid management system 10 may optionally include a flow sensor in place of, or in addition to, each of the pressure sensor(s) 74. In some embodiments, the fluid management system 10 may optionally include a load sensor in place of, or in addition to, each of the pressure sensor(s) 74 and/or the flow sensor(s).

In some embodiments, the handle of the medical device 20 may include a port 86 configured to receive the elongate tubular member 116 of the laser device 100. In some embodiments, the laser device 100 may be connected to and/or secured to the port 86. In some embodiments, the port 86 may be in fluid communication with a working lumen of the medical device 20 and/or the elongate shaft 76.

In some embodiments, the laser controller 110 (e.g., FIG. 3) may be in electronic communication with the controller 30 of the fluid management system 10. In some embodiments, the laser controller 110 may be configured to cooperate with, coordinate with, and/or work together with the controller 30 of the fluid management system 10 to manage operation and/or function(s) of the medical system during use. In some embodiments, the laser controller 110 may delay activation of laser power until after the controller 30 of the fluid management system 10 activates the cooling pump 53. In some embodiments, when the laser controller 110 increases laser power, the controller 30 of the fluid management system may speed up the cooling pump 53, increase fluid flow through and/or coming out of the cooling pump 53, and/or increase fluid pressure output by the cooling pump 53. In some embodiments, when the laser controller 110 terminates laser power, the controller 30 of the fluid management system 10 may shut down the cooling pump 53. Other configurations are also contemplated.

In some embodiments, the laser controller 110 may monitor a temperature of the distal end of the laser fiber 114 and/or the elongate tubular member 116 and instruct the controller 30 of the fluid management system 10 to increase the speed of the cooling pump 53 and/or the fluid flow rate and/or fluid pressure output by the cooling pump 53 if the temperature exceeds a predetermined limit. In some embodiments, the controller 30 of the fluid management system may monitor a temperature of the distal end of the elongate tubular member 116 and/or the elongate shaft 76 and increase the speed of the cooling pump 53 and/or the fluid flow rate and/or fluid pressure output by the cooling pump 53 if the temperature exceeds a predetermined limit.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

The materials that can be used for the various components of the system(s) and the various elements thereof disclosed herein may include those commonly associated with medical devices. For simplicity purposes, the following discussion refers to the system. However, this is not intended to limit the devices and methods described herein, as the discussion may be applied to other elements, members, components, or devices disclosed herein, such as, but not limited to, the fluid management system, the medical device, the laser device, the elongate shaft, the elongate tubular member, the laser fiber, the inflow pump, the outflow pump, the cooling pump, the fluid warming system, the controller, the laser controller, the supply line(s), the load cells, the handle, the workstation, the display screen(s), the fluid supply source(s), the collection container(s), and/or elements or components thereof.

In some embodiments, the system, and/or components thereof, may be made from a metal, metal alloy, polymer (some examples of which are disclosed below), a metal-polymer composite, ceramics, combinations thereof, and the like, or other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), MARLEX® high-density polyethylene, MARLEX® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, polyurethane silicone copolymers (for example, Elast-Eon® from AorTech Biomaterials or ChronoSil® from AdvanSource Biomaterials), biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; platinum; palladium; gold; combinations thereof; or any other suitable material.

In at least some embodiments, portions or all of the system, and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the system in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the system to achieve the same result.

In some embodiments, a degree of Magnetic Resonance Imaging (MM) compatibility is imparted into the system and/or other elements disclosed herein. For example, the system, and/or components or portions thereof, may be made of a material that does not substantially distort the image and create substantial artifacts (i.e., gaps in the image). Certain ferromagnetic materials, for example, may not be suitable because they may create artifacts in an Mill image. The system, or portions thereof, may also be made from a material that the Mill machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

In some embodiments, the system and/or other elements disclosed herein may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethyl ketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl ketone, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A medical system, comprising:
   an endoscope comprising:
      an elongate shaft configured to access a treatment site within a patient; and
      a handle coupled to a proximal end of the elongate shaft;
   a laser device including an elongate tubular member configured for insertion through a working lumen of the elongate shaft of the endoscope, the elongate tubular member including a cooling channel and a laser fiber extending distally within the cooling channel; and
   a fluid management system comprising:
      an inflow pump configured to pump fluid from a first fluid supply source through the elongate shaft to the treatment site;

a cooling pump configured to pump fluid from a second fluid supply source through the cooling channel; and
a controller configured to control the inflow pump and the cooling pump.

2. The medical system of claim 1, wherein the cooling pump is a peristaltic pump.

3. The medical system of claim 1, wherein the cooling pump is a diaphragm pump.

4. The medical system of claim 1, wherein the cooling pump is a positive displacement pump.

5. The medical system of claim 1, wherein the cooling pump includes a disposable, single-use pump head.

6. The medical system of claim 1, wherein the fluid management system includes a pressure sensor disposed between the cooling pump and a distal end of the cooling channel.

7. The medical system of claim 1, wherein the fluid management system includes a pressure sensor disposed between the second fluid supply source and the cooling pump.

8. The medical system of claim 1, wherein the cooling pump is configured to pump fluid through the cooling channel at a fluid flow rate between 0 mL/minute and 100 mL/minute.

9. The medical system of claim 1, wherein the cooling pump is configured to pump fluid through the cooling channel at a fluid pressure between 0 mmHg and 500 mmHg.

10. A medical system, comprising:
an endoscope comprising:
an elongate shaft configured to access a treatment site within a patient; and
a handle coupled to a proximal end of the elongate shaft;
a laser device including an elongate tubular member configured for insertion through a working lumen of the elongate shaft of the endoscope, the elongate tubular member including a cooling channel and a laser fiber extending distally within the cooling channel; and
a fluid management system comprising:
an inflow pump configured to pump fluid from a first fluid supply source through the elongate shaft to the treatment site;
a cooling pump configured to pump fluid from a second fluid supply source through the cooling channel; and
a controller configured to control the inflow pump and the cooling pump;
wherein the laser device includes a laser controller in electronic communication with the controller of the fluid management system.

11. The medical system of claim 10, wherein when the laser controller increases laser power, the controller of the fluid management system speeds up the cooling pump.

12. The medical system of claim 10, wherein when the laser controller terminates laser power, the controller of the fluid management system shuts down the cooling pump.

13. The medical system of claim 10, wherein the laser controller delays activation of laser power until after the controller of the fluid management system activates the cooling pump.

14. The medical system of claim 10, wherein the laser controller monitors a temperature of a distal end of the laser fiber and instructs the controller of the fluid management system to increase cooling pump speed if the temperature exceeds a predetermined limit.

15. A medical system, comprising:
an endoscope comprising:
an elongate shaft configured to access a treatment site within a patient; and
a handle coupled to a proximal end of the elongate shaft;
a laser device including an elongate tubular member configured for insertion through a working lumen of the elongate shaft of the endoscope, the elongate tubular member including a cooling channel and a laser fiber extending distally within the cooling channel such that the cooling channel coaxially surrounds the laser fiber; and
a fluid management system comprising:
an inflow pump configured to pump fluid from a first fluid supply source through the elongate shaft to the treatment site;
a cooling pump configured to pump fluid from a second fluid supply source through the cooling channel; and
a controller configured to control the inflow pump and the cooling pump;
wherein the laser device includes a laser controller in electronic communication with the controller of the fluid management system.

16. The medical system of claim 15, wherein the cooling channel terminates at a distal port proximal a distal end of the elongate tubular member.

17. The medical system of claim 16, wherein laser energy exits the elongate tubular member through the distal port.

18. The medical system of claim 15, wherein the laser device includes a handle portion at a proximal end of the elongate tubular member, the handle portion being configured to rotate the elongate tubular member.

19. The medical system of claim 15, wherein the controller of the fluid management system is configured to control the cooling pump to maintain a target fluid flow rate through the cooling channel based on a set of system operating parameters.

20. The medical system of claim 15, wherein the controller of the fluid management system is configured to control the cooling pump to maintain a target fluid pressure through the cooling channel based on a set of system operating parameters.

* * * * *